(12) United States Patent
Shoji et al.

(10) Patent No.: US 7,498,583 B2
(45) Date of Patent: Mar. 3, 2009

(54) RADIATION IMAGING APPARATUS

(75) Inventors: Takashi Shoji, Kanagawa-ken (JP); Masakazu Nakajo, Kanagawa-ken (JP)

(73) Assignee: Fujifilm Corporation, Tokyo (JP)

( * ) Notice: Subject to any disclaimer, the term of this patent is extended or adjusted under 35 U.S.C. 154(b) by 220 days.

(21) Appl. No.: 11/393,838

(22) Filed: Mar. 31, 2006

(65) Prior Publication Data

US 2006/0219926 A1    Oct. 5, 2006

(30) Foreign Application Priority Data

Mar. 31, 2005   (JP)   ............... 2005-103778

(51) Int. Cl.
*G01T 1/24* (2006.01)
(52) U.S. Cl. .................. 250/370.09; 250/580
(58) Field of Classification Search ............ 250/370.09, 250/580
See application file for complete search history.

(56) References Cited

U.S. PATENT DOCUMENTS

| | | | |
|---|---|---|---|
| 5,105,087 A * | 4/1992 | Jagielinski | ............. 250/370.09 |
| 5,661,309 A | 8/1997 | Jeromin et al. | |
| 6,268,614 B1 | 7/2001 | Imani | |
| 6,828,539 B1 | 12/2004 | Kuwabara | |
| 2004/0101103 A1 * | 5/2004 | Warp et al. | ............... 378/98.12 |

\* cited by examiner

*Primary Examiner*—David P Porta
*Assistant Examiner*—Mark R Gaworecki
(74) *Attorney, Agent, or Firm*—Sughrue Mion, PLLC (57) ABSTRACT

Radiation detector units provided with solid-state radiation detectors are supported on a supporting section, such that the radiation detector units are located at different distances from a radiation source and arrayed in a one-dimensional direction or two-dimensional directions. One of the radiation detector units is taken as a reference unit. Image size enlargement or reduction processing is performed on each of image signals outputted from the radiation detector units other than the reference unit and in accordance with a ratio between a distance from the radiation source to the reference unit and a distance from the radiation source to each of the radiation detector units other than the reference unit. Image composing processing is performed on the image signal outputted from the reference unit and processed image signals obtained from the image size enlargement or reduction processing.

5 Claims, 4 Drawing Sheets

RADIATION IMAGING APPARATUS

BACKGROUND OF THE INVENTION

1. Field of the Invention

This invention relates to a radiation imaging apparatus, wherein an imaging operation is performed by use of an array of a plurality of radiation detector units, each of which is provided with a solid-state radiation detector, wherein image composing processing is performed on image signals, each of which is outputted from one of the radiation detector units, and in accordance with the array of the plurality of the radiation detector units, and wherein a composed image signal is thereby acquired.

2. Description of the Related Art

With respect to X-ray (radiation) imaging operations for medical diagnoses, and the like, various X-ray imaging apparatuses, in which solid-state radiation detectors (utilizing semiconductors as principal sections) are utilized as X-ray image information recording means, have heretofore been proposed and used in practice. With each of the X-ray imaging apparatuses described above, X-rays carrying image information of an object is detected by the solid-state radiation detector, and an image signal representing an X-ray image of the object is thereby obtained.

As for the solid-state radiation detectors to be utilized in the X-ray imaging apparatuses, various types of solid-state radiation detectors have heretofore been proposed. For example, from the view point of an electric charge forming process for converting the X-rays into electric charges, the solid-state radiation detectors may be classified into a photo conversion type of solid-state radiation detector and a direct conversion type of solid-state radiation detector. With the photo conversion type of the solid-state radiation detector, fluorescence, which has been produced by a fluorescent substance when X-rays have been irradiated to the fluorescent substance, is detected by a photo-conductor layer, and signal electric charges having thus been generated in the photo-conductor layer are accumulated at a charge accumulating section. Also, the signal electric charges having thus been accumulated at the charge accumulating section are converted into an image signal (an electric signal), and the thus obtained image signal is outputted from the solid-state radiation detector. With the direct conversion type of the solid-state radiation detector, signal electric charges, which have been generated in a photo-conductor layer when the X-rays have been irradiated to the photo-conductor layer, are collected with a charge collecting electrode and accumulated at a charge accumulating section, the signal electric charges having thus been accumulated at the charge accumulating section are converted into an electric signal, and the thus obtained electric signal is outputted from the solid-state radiation detector. In the direct conversion type of the solid-state radiation detector, the photo-conductor layer and the charge collecting electrode constitute a principal section.

Also, from the view point of an electric charge read-out process for reading out the accumulated electric charges to the exterior, the solid-state radiation detectors may be classified into an optical read-out type of solid-state radiation detector and a thin-film transistor (TFT) read-out type of solid-state radiation detector. With the optical read-out type of the solid-state radiation detector, reading light (a reading electromagnetic wave) is irradiated to the solid-state radiation detector, and electric charges having been accumulated are thereby read out. With the TFT read-out type of the solid-state radiation detector, TFT's connected to a charge accumulating section are actuated successively, and electric charges having been accumulated are thereby read out. (The TFT read-out type of the solid-state radiation detector is described in, for example, U.S. Pat. No. 6,828,539.)

The applicant proposed an improved direct conversion type of solid-state radiation detector in, for example, U.S. Pat. No. 6,268,614. The improved direct conversion type of the solid-state radiation detector is a direct conversion type and optical read-out type of a solid-state radiation detector. The improved direct conversion type of the solid-state radiation detector comprises a recording photo-conductor layer, which is capable of exhibiting photo-conductivity when recording light (the X-rays, the fluorescence produced through irradiation of the X-rays, or the like) is irradiated to the recording photo-conductor layer. The improved direct conversion type of the solid-state radiation detector also comprises a charge transporting layer, which acts approximately as an electrical insulator with respect to electric charges having a polarity identical with the polarity of latent image charges, and which acts approximately as an electrical conductor with respect to transported electric charges having a polarity opposite to the polarity of the latent image charges. The improved direct conversion type of the solid-state radiation detector further comprises a reading photo-conductor layer, which is capable of exhibiting the photo-conductivity when a reading electromagnetic wave is irradiated to the reading photo-conductor layer. The recording photo-conductor layer, the charge transporting layer, and the reading photo-conductor layer are overlaid in this order. The signal electric charges (i.e., the latent image charges) carrying image information are accumulated at an interface (i.e., a charge accumulating section) between the recording photo-conductor layer and the charge transporting layer. Also, electrodes (i.e., a first electrical conductor layer and a second electrical conductor layer) are formed on opposite sides of the combination of the three layers described above. In the improved direct conversion type of the solid-state radiation detector, the recording photo-conductor layer, the charge transporting layer, and the reading photo-conductor layer constitute a principal section.

Further, there have heretofore been proposed various radiation detecting cassettes (i.e., radiation detector units) comprising a case housing, in which a solid-state radiation detector, an electric power source, and the like, are accommodated. (A radiation detecting cassette is described in, for example, U.S. Pat. No. 5,661,309.) The radiation detecting cassettes are comparatively thin and have a size enabling conveyance. Therefore, with the radiation detecting cassettes, imaging operations are capable of being performed with a high flexibility. For example, with respect to a patient who is not capable of moving, it is possible to perform the imaging operation, wherein the patient is allowed to lie down on a bed, the radiation detecting cassette is located under a site, the image of which is to be recorded, and a radiation source of a radiation imaging apparatus is moved to a position above the patient, which position stands facing the radiation detecting cassette. Also, the radiation detecting cassette is capable of being loaded into an imaging apparatus, such as a mamma image recording and read-out apparatus, and an imaging operation is capable of being performed in this state.

In the field of the radiation imaging, it is often desired that the imaging operation is capable of being performed on an object having a markedly large area as in the cases of general vertebral column imaging operation, general lower extremity imaging operation, or the like. However, in cases where the imaging operation on the object having a markedly large area is to be performed by use of the radiation detecting cassette, the imaging range is not capable of being covered with one radiation detecting cassette. Therefore, in such cases, it may be considered that the imaging operation is performed by use of a plurality of radiation detecting cassettes, which are arrayed in a one-dimensional direction or two-dimensional directions, and that the image signals having been outputted from the plurality of the radiation detecting cassettes are combined with one another in accordance with the array of the radiation detecting cassettes.

However, ordinarily, the solid-state radiation detector is not capable of being located over the entire area of a radiation irradiation surface of each of the radiation detecting cassettes. Therefore, in cases where the imaging operation is to be performed by use of the plurality of the radiation detecting cassettes arrayed in the manner described above, if the plurality of the radiation detecting cassettes are arrayed on an identical plane, the image information corresponding to joint sections of the radiation detecting cassettes will not be capable of being acquired. Accordingly, it is necessary that the radiation detecting cassettes are located at different distances from the radiation source, such that end regions of adjacent radiation detecting cassettes may overlap each other, and such that all of the image information corresponding to the imaging range may be capable of being acquired.

However, if the radiation detecting cassettes are located at different distances from the radiation source, the image size of the obtained object image will vary for different radiation detecting cassettes, and an image will not be capable of being composed accurately.

SUMMARY OF THE INVENTION

The primary object of the present invention is to provide a radiation imaging apparatus, wherein an imaging operation is performed by use of an array of a plurality of radiation detector units, each of which is provided with a solid-state radiation detector, wherein image composing processing is performed on image signals, each of which is outputted from one of the radiation detector units, and in accordance with the array of the plurality of the radiation detector units, and wherein a composed image signal is thereby acquired, the radiation imaging apparatus being capable of acquiring all of image information corresponding to an imaging range without omission and capable of composing an image accurately.

The present invention provides a radiation imaging apparatus, comprising:

i) a plurality of radiation detector units, each of which is provided with a solid-state radiation detector, the solid-state radiation detector being capable of recording image information when radiation carrying the image information is irradiated to the solid-state radiation detector, the solid-state radiation detector being capable of outputting an image signal representing the image information having been recorded in the solid-state radiation detector, ii) a radiation detector unit supporting section for supporting the plurality of the radiation detector units in a state, in which the plurality of the radiation detector units are located at different distances from a radiation source for irradiating the radiation to the plurality of the radiation detector units and are arrayed in a one-dimensional direction or in two-dimensional directions, and iii) image composing means for performing image composing processing on the image signals, which have been outputted from the plurality of the radiation detector units, and in accordance with the array of the plurality of the radiation detector units, and thereby acquiring a composed image signal, the image composing means taking one radiation detector unit, which is among the plurality of the radiation detector units, as a reference unit, performing image size enlargement or reduction processing on each of the image signals, which have been outputted from the radiation detector units other than the reference unit, and in accordance with a ratio between a distance from the radiation source to the reference unit and a distance from the radiation source to each of the radiation detector units other than the reference unit, and thereafter performing the image composing processing on the image signal, which has been outputted from the reference unit, and processed image signals, which have been obtained from the image size enlargement or reduction processing having been performed on the image signals having been outputted from the radiation detector units other than the reference unit.

The term "solid-state radiation detector" as used herein means the detector, which is capable of detecting the radiation carrying the image information of an object and is capable of outputting the image signal representing the radiation image of the object. The solid-state radiation detector is capable of converting the incident radiation into electric charges directly or after converting the incident radiation into light and is capable of outputting the electric charges to the exterior. With the solid-state radiation detector, the image signal representing the radiation image of the object is thus capable of being acquired.

The solid-state radiation detector may be one of various types of solid-state radiation detectors. For example, from the view point of an electric charge forming process for converting the radiation into the electric charges, the solid-state radiation detectors may be classified into a photo conversion type of solid-state radiation detector and a direct conversion type of solid-state radiation detector. With the photo conversion type of the solid-state radiation detector, the fluorescence, which has been produced by a fluorescent substance when the radiation has been irradiated to the fluorescent substance, is detected by a photo-conductor layer, and the signal electric charges having thus been generated in the photo-conductor layer are accumulated at a charge accumulating section. Also, the signal electric charges having thus been accumulated at the charge accumulating section are converted into an image signal (an electric signal), and the thus obtained image signal is outputted from the solid-state radiation detector. With the direct conversion type of the solid-state radiation detector, the signal electric charges, which have been generated in a photo-conductor layer when the radiation has been irradiated to the photo-conductor layer, are collected with a charge collecting electrode and accumulated at a charge accumulating section, the signal electric charges having thus been accumulated at the charge accumulating section are converted into an electric signal, and the thus obtained electric signal is outputted from the solid-state radiation detector. Also, from the view point of an electric charge read-out process for reading out the accumulated electric charges to the exterior, the solid-state radiation detectors may be classified into an optical read-out type of solid-state radiation detector and a thin-film transistor (TFT) read-out type of solid-state radiation detector. With the optical read-out type of the solid-state radiation detector, reading light (a reading electromagnetic wave) is irradiated to the solid-state radiation detector, and electric charges having been accumulated are thereby read out. With the TFT read-out type of the solid-state radiation detector, TFT's connected to a charge accumulating section are actuated successively, and electric charges having been accumulated are thereby read out. The solid-state radiation detector may also be an improved direct conversion type of solid-state radiation detector, which has been proposed by the applicant in, for example, U.S. Pat. No. 6,268,614. The improved direct conversion type of the solid-state radiation detector is constituted of a combination of the direct conversion type and the optical read-out type.

The radiation imaging apparatus in accordance with the present invention should preferably be modified such that the radiation detector unit supporting section is provided with position adjusting means for adjusting the positions of the radiation detector units with respect to one another.

In such cases, the radiation imaging apparatus in accordance with the present invention should more preferably be modified such that each of the radiation detector units is provided with a radiation absorbing member for indicating a reference position, which radiation absorbing member is located at an area in the vicinity of an outside periphery of the solid-state radiation detector constituting the radiation detector unit.

The term "area in the vicinity of an outside periphery" as used herein means the area in the radiation detector unit, which area overlaps upon the area in the adjacent radiation detector unit in cases where the plurality of the radiation detector units are located at different distances from the radiation source, such that end regions of the adjacent radiation detector units may overlap each other.

The radiation imaging apparatus in accordance with the present invention comprises: (i) the plurality of the radiation detector units, each of which is provided with the solid-state radiation detector, the solid-state radiation detector being capable of recording the image information when the radiation carrying the image information is irradiated to the solid-state radiation detector, the solid-state radiation detector being capable of outputting the image signal representing the image information having been recorded in the solid-state radiation detector, (ii) the radiation detector unit supporting section for supporting the plurality of the radiation detector units in the state, in which the plurality of the radiation detector units are located at different distances from the radiation source for irradiating the radiation to the plurality of the radiation detector units and are arrayed in a one-dimensional direction or in two-dimensional directions, and (iii) the image composing means for performing the image composing processing on the image signals, which have been outputted from the plurality of the radiation detector units, and in accordance with the array of the plurality of the radiation detector units, and thereby acquiring the composed image signal. The image composing means takes one radiation detector unit, which is among the plurality of the radiation detector units, as the reference unit. Also, the image composing means performs the image size enlargement or reduction processing on each of the image signals, which have been outputted from the radiation detector units other than the reference unit, and in accordance with the ratio between the distance from the radiation source to the reference unit and the distance from the radiation source to each of the radiation detector units other than the reference unit. Further, the image composing means performs the image composing processing on the image signal, which has been outputted from the reference unit, and the processed image signals, which have been obtained from the image size enlargement or reduction processing having been performed on the image signals having been outputted from the radiation detector units other than the reference unit. Therefore, with the radiation imaging apparatus in accordance with the present invention, in cases where the plurality of the radiation detector units are located at different distances from the radiation source and are arrayed, such that the end regions of the adjacent radiation detector units overlap each other and such that all of the image information in the imaging range is capable of being acquired without omission, an image is capable of being composed accurately.

With the radiation imaging apparatus in accordance with the present invention, wherein the radiation detector unit supporting section is provided with the position adjusting means for adjusting the positions of the radiation detector units with respect to one another, it is possible to make the position adjustments, such as correction of inclination and correction of shift, with respect to the solid-state radiation detectors constituting the radiation detector units.

With the radiation imaging apparatus in accordance with the present invention, wherein each of the radiation detector units is provided with the radiation absorbing member for indicating the reference position, which radiation absorbing member is located at the area in the vicinity of the outside periphery of the solid-state radiation detector constituting the radiation detector unit, the position adjustments, such as the correction of the inclination and the correction of the shift, with respect to the solid-state radiation detectors constituting the radiation detector units are capable of being made easily in accordance with the shift of the reference positions at the region, at which the two adjacent solid-state radiation detectors overlap each other, in the recorded images.

DESCRIPTION OF THE PREFERRED EMBODIMENTS

The present invention will hereinbelow be described in further detail with reference to the accompanying drawings.

Figure 1:
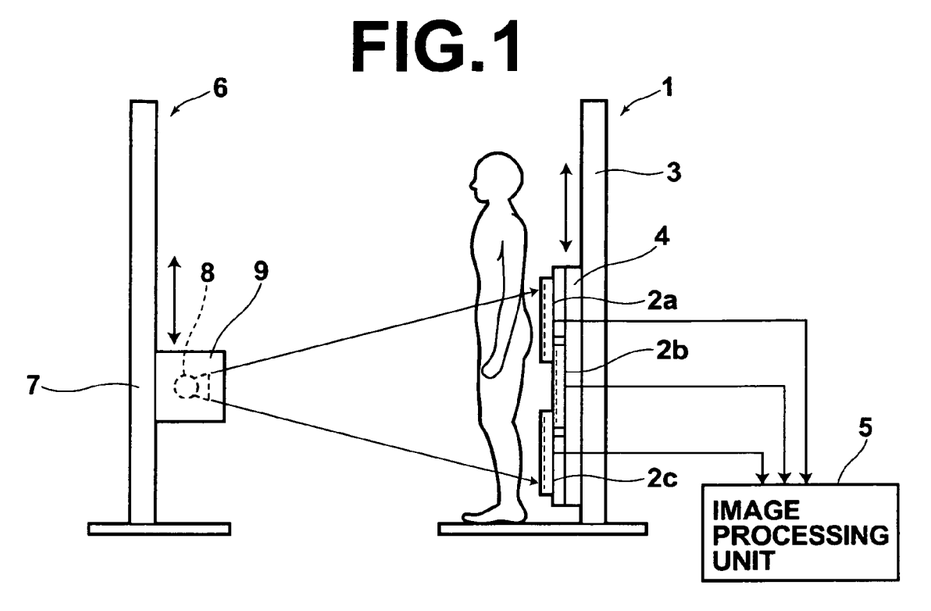
FIG. 1 is a schematic view showing an X-ray imaging apparatus, which is an embodiment of the radiation imaging apparatus in accordance with the present invention.
Figure 2:
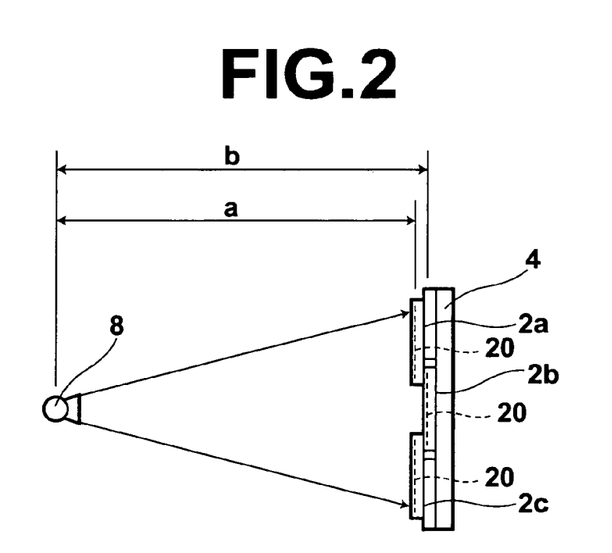
FIG. 2 is an explanatory view showing relationship between a position of each of radiation detector units of the X-ray imaging apparatus shown in FIG. 1 and a position of an X-ray source.
Figure 3:
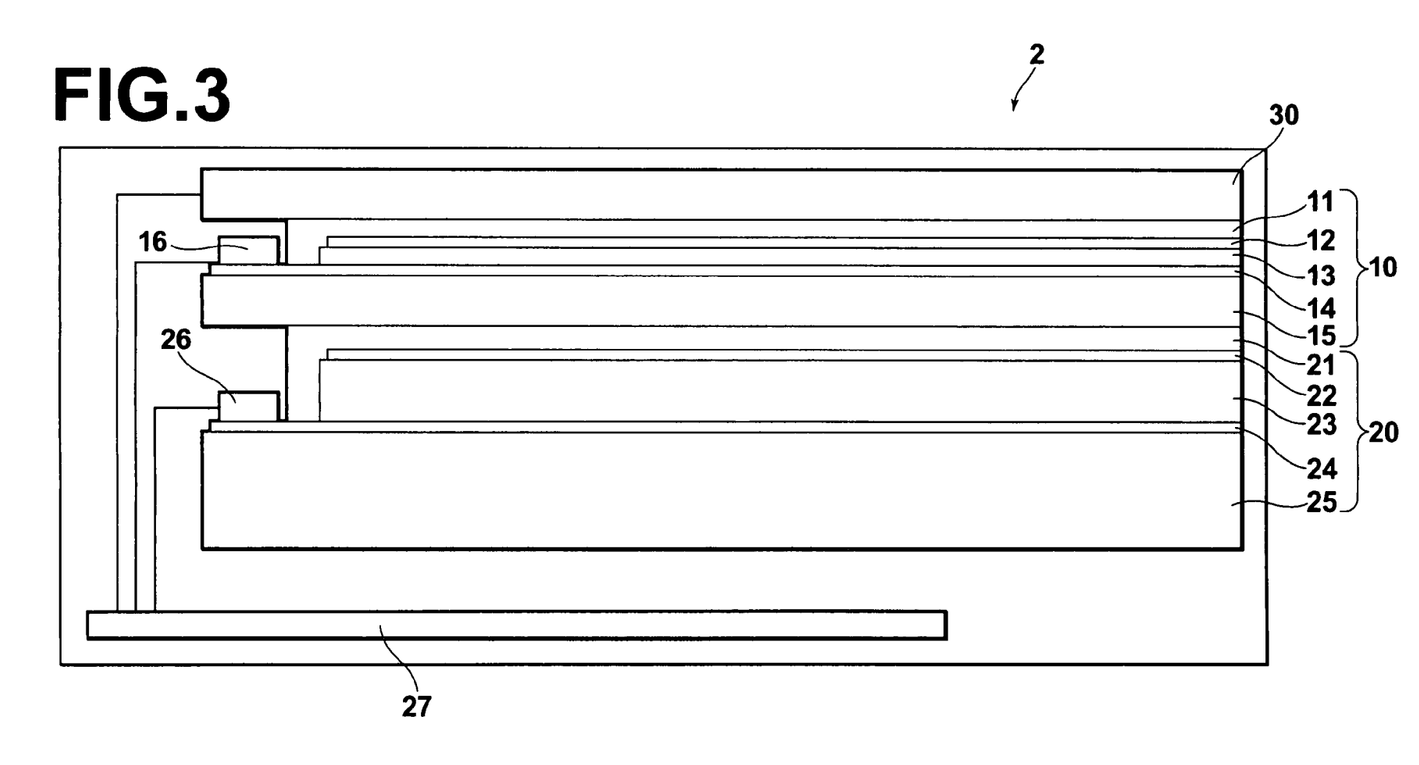
FIG. 3 is a schematic view showing a constitution in each of the radiation detector units of the X-ray imaging apparatus shown in FIG. 1.
Figure 4:
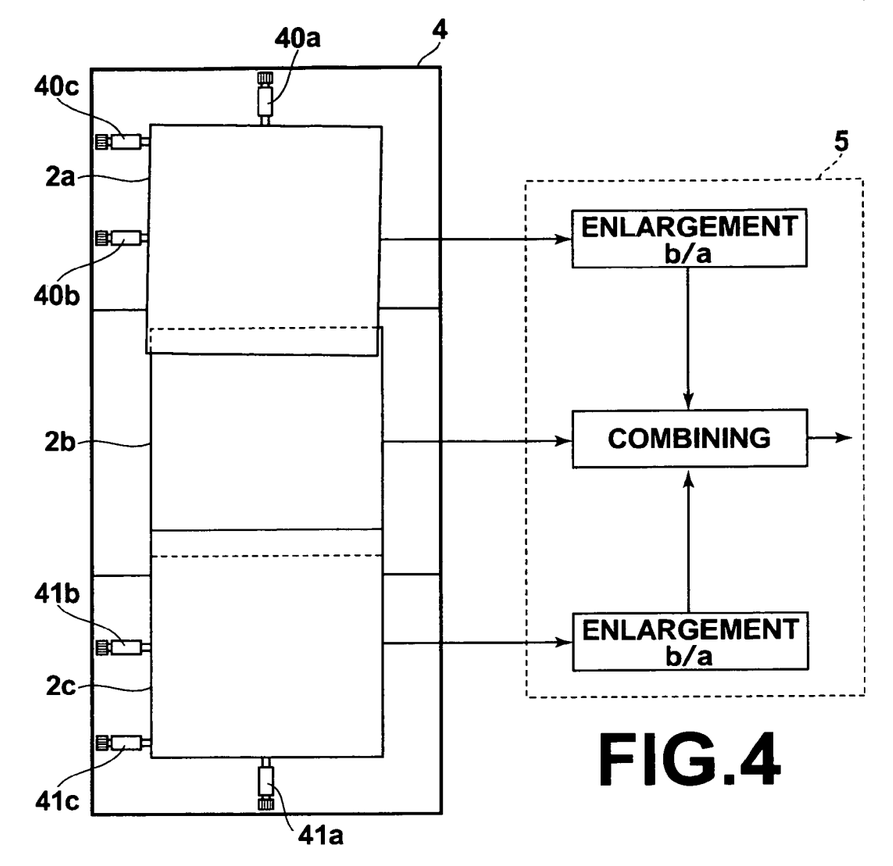
FIG. 4 is a front view showing a radiation detector unit supporting section of the X-ray imaging apparatus shown in FIG. 1.
Figure 5:
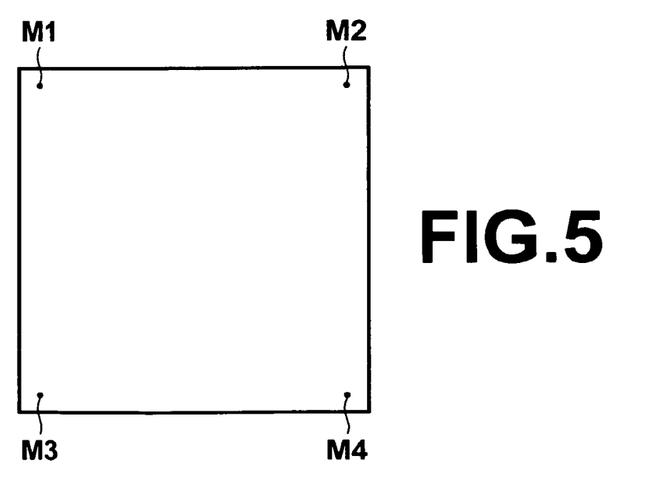
FIG. 5 is an explanatory view showing locations of markers (radiation absorbing members) in each of the radiation detector units.

FIG. 1 is a schematic view showing an X-ray imaging apparatus, which is an embodiment of the radiation imaging apparatus in accordance with the present invention. FIG. 2 is an explanatory view showing relationship between a position of each of radiation detector units of the X-ray imaging apparatus shown in FIG. 1 and a position of an X-ray source. FIG. 3 is a schematic view showing a constitution in each of the radiation detector units of the X-ray imaging apparatus shown in FIG. 1. FIG. 4 is a front view showing a radiation detector unit supporting section of the X-ray imaging apparatus shown in FIG. 1. FIG. 5 is an explanatory view showing locations of markers (radiation absorbing members) in each of the radiation detector units.

With reference to FIG. 1, an X-ray imaging apparatus 1 comprises three radiation detector units (i.e., cassettes) 2a, 2b, and 2c, each of which accommodates a solid-state radiation detector 20 therein. The X-ray imaging apparatus 1 also comprises a radiation detector unit supporting section 4 for supporting the radiation detector units 2a, 2b, and 2c. The X-ray imaging apparatus 1 further comprises abase 3 for supporting the radiation detector unit supporting section 4 such that the radiation detector unit supporting section 4 is capable of moving vertically. The X-ray imaging apparatus 1 still further comprises an image processing unit 5, which is connected to each of the radiation detector units 2a, 2b, and 2c.

The image processing unit 5 acts as image composing means for performing image composing processing on image signals, each of which is outputted from one of the radiation detector units 2a, 2b, and 2c. The image processing unit 5 also acts as control means for controlling each of the radiation detector units 2a, 2b, and 2c.

An X-ray irradiating apparatus 6 irradiates X-rays to the X-ray imaging apparatus 1. The X-ray irradiating apparatus 6 comprises an X-ray source accommodating section 9, in which an X-ray source 8 is accommodated. The X-ray irradiating apparatus 6 also comprises a base 7 for supporting the X-ray source accommodating section 9 such that the X-ray source accommodating section 9 is capable of moving vertically.

The radiation detector units 2a, 2b, and 2c have an identical constitution. As illustrated in FIG. 3, an X-ray quantity detector 10 for detecting the X-ray quantity irradiated to the radiation detector unit 2 (i.e., each of the radiation detector units 2a, 2b, and 2c) is located within a case housing of the radiation detector unit 2. Also, the solid-state radiation detector 20 acting as an imaging device is located within the case housing of the radiation detector unit 2. Further, a moving grid 30 for removing scattered X-rays is located within the case housing of the radiation detector unit 2. Furthermore, a printed circuit board 27, which is provided with control means for controlling the X-ray quantity detector 10, the solid-state radiation detector 20, and the moving grid 30, is located within the case housing of the radiation detector unit 2. Also, an electric power source (not shown) for supplying an electric power to the X-ray quantity detector 10, the solid-state radiation detector 20, the moving grid 30, and the printed circuit board 27 is located within the case housing of the radiation detector unit 2.

The X-ray quantity detector 10 comprises a resin base plate 15. The X-ray quantity detector 10 also comprises a first electrical conductor layer 14, a photo-conductor layer 13, which generates electric charges and exhibits the electrical conductivity when the X-rays are irradiated to the photo-conductor layer 13, a second electrical conductor layer 12, and an electrical insulation layer 11, the layers being overlaid in this order on the resin base plate 15.

With the X-ray quantity detector 10, in cases where the X-rays are irradiated to the photo-conductor layer 13, while an electric field is being formed across the first electrical conductor layer 14 and the second electrical conductor layer 12, pairs of positive and negative charges are generated in the photo-conductor layer 13, and an electric current proportional to the quantity of the pairs of positive and negative charges flows across the first electrical conductor layer 14 and the second electrical conductor layer 12. The electric current flowing across the first electrical conductor layer 14 and the second electrical conductor layer 12 is converted by an IC chip 16 into a voltage.

The signal outputted from the IC chip 16 is integrated by an integration circuit (not shown) of the printed circuit board 27. Also, a comparison circuit (not shown) of the printed circuit board 27 makes a comparison between the voltage, which has been obtained from the integration performed by the integration circuit, and a predetermined value. In cases where the voltage, which has been obtained from the integration performed by the integration circuit, has become higher than the predetermined value, information representing that the voltage, which has been obtained from the integration performed by the integration circuit, has become higher than the predetermined value is outputted. In this manner, it is possible to judge that the quantity of the X-rays irradiated to the radiation detector unit 2 has become higher than the predetermined value.

The solid-state radiation detector 20 comprises a glass base plate 25. The solid-state radiation detector 20 also comprises a first electrical conductor layer 24, which is constituted of a-Si TFT's, a photo-conductor layer 23, which generates electric charges and exhibits the electrical conductivity when the X-rays are irradiated to the photo-conductor layer 23, a second electrical conductor layer 22, and an electrical insulation layer 21, the layers being overlaid in this order on the glass base plate 25. Also, as illustrated in FIG. 5, a marker (i.e., a radiation absorbing member) Ml is formed on an upper left corner area of the electrical insulation layer 21, and a marker M2 is formed on an upper right corner area of the electrical insulation layer 21. Further, a marker M3 is formed on a lower left corner area of the electrical insulation layer 21, and a marker M4 is formed on a lower right corner area of the electrical insulation layer 21.

The first electrical conductor layer 24 is provided with the TFT's, each of which corresponds to one of pixels. The outputs of the TFT's are connected to an IC chip 26. The IC chip 26 is connected to the printed circuit board 27, which is provided with an analog-to-digital converting section (not shown), a memory (not shown), and the like.

With the solid-state radiation detector 20, in cases where the X-rays are irradiated to the photo-conductor layer 23, while an electric field is being formed across the first electrical conductor layer 24 and the second electrical conductor layer 22, pairs of positive and negative charges are generated in the photo-conductor layer 23. Latent image charges proportional to the quantity of the pairs of the positive and negative charges are accumulated in the first electrical conductor layer 24. In cases where the thus accumulated latent image charges are to be readout, the TFT's of the first electrical conductor layer 24 are actuated successively, and the latent image charges corresponding to the respective pixels are read out. In this manner, an electrostatic latent image carried by the latent image charges is capable of being read out.

The X-ray quantity detector 10 is overlaid on the solid-state radiation detector 20 such that, in cases where the radiation detector unit 2 is supported on the radiation detector unit supporting section 4, the X-ray quantity detector 10 intervenes between the X-ray source 8 and the solid-state radiation detector 20. Therefore, the X-ray quantity detector 10 is capable of directly detecting the X-rays, which have been radiated out from the X-ray source 8, before the X-rays impinge upon the solid-state radiation detector 20. Accordingly, the quantity of the X-rays is capable of being measured accurately without the measurement being affected by the solid-state radiation detector 20.

The control means on the side of the radiation detector unit 2 controls the X-ray quantity detector 10, the solid-state radiation detector 20, the moving grid 30, and the like, in accordance with instruction signals given by the image processing unit 5. The control means on the side of the radiation detector unit 2 thus performs the control for the acquisition of an X-ray image.

As illustrated in FIG. 2 and FIG. 4, the radiation detector units 2a, 2b, and 2c are arrayed in the vertical one-dimensional direction, such that the solid-state radiation detectors 20, 20, which are accommodated in the adjacent radiation detector units 2, 2 among the radiation detector units 2a, 2b, and 2c, may overlap each other, and such that all of the image information in the imaging range may be acquired without omission. The radiation detector units 2a, 2b, and 2c are supported in the arrayed state on the radiation detector unit supporting section 4. Specifically, the radiation detector unit 2b is supported at the middle position with respect to the vertical array direction. The radiation detector unit 2a is supported on a surface, which is shifted from the support surface for the radiation detector unit 2b toward the side of the X-ray source 8, such that the bottom end region of the radiation detector unit 2a may overlap upon the top end region of the radiation detector unit 2b. The radiation detector unit 2c is supported on a surface, which is shifted from the support surface for the radiation detector unit 2b toward the side of the X-ray source 8, such that the top end region of the radiation detector unit 2c may overlap upon the bottom end region of the radiation detector unit 2b.

The radiation detector unit 2a is urged in the direction heading toward the upper left corner at the radiation detector unit supporting section 4. Also, the radiation detector unit supporting section 4 is provided with dial meters 40a, 40b, and 40c, which act as position adjusting means for adjusting the position of the radiation detector unit 2a. The dial meter 40a is located such that the dial meter 40a may be in contact with the area in the vicinity of the middle of the top side face of the radiation detector unit 2a. The dial meter 40b is located such that the dial meter 40b may be in contact with the area in the vicinity of the middle of the left side face of the radiation detector unit 2a. Also, the dial meter 40c is located such that the dial meter 40c may be in contact with the area in the vicinity of the top of the left side face of the radiation detector unit 2a. Therefore, with the adjustments of the dial meters 40a, 40b, and 40c, the radiation detector unit 2a is capable of being moved vertically and horizontally and is capable of being rotated.

The radiation detector unit 2c is urged in the direction heading toward the lower left corner at the radiation detector unit supporting section 4. Also, the radiation detector unit supporting section 4 is provided with dial meters 41a, 41b, and 41c, which act as the position adjusting means for adjusting the position of the radiation detector unit 2c. The dial meter 41a is located such that the dial meter 41a may be in contact with the area in the vicinity of the middle of the bottom side face of the radiation detector unit 2c. The dial meter 41b is located such that the dial meter 41b may be in contact with the area in the vicinity of the middle of the left side face of the radiation detector unit 2c. Also, the dial meter 41c is located such that the dial meter 41c may be in contact with the area in the vicinity of the bottom of the left side face of the radiation detector unit 2c. Therefore, with the adjustments of the dial meters 41a, 41b, and 41c, the radiation detector unit 2c is capable of being moved vertically and horizontally and is capable of being rotated.

In the X-ray imaging apparatus 1 having the constitution described above, the distance from the X-ray source 8 to each of the radiation detector units 2a and 2c (which distance is represented by the double-headed arrow "a" in FIG. 2) and the distance from the X-ray source 8 to the radiation detector unit 2b (which distance is represented by the double-headed arrow "b" in FIG. 2) are different from each other. Therefore, in cases where the X-ray imaging operation is performed by use of the X-ray imaging apparatus 1, an image size of an object image, which is recorded with each of the radiation detector units 2a and 2c, and the image size of the object image, which is recorded with the radiation detector unit 2b, are different from each other. If the image composing processing is performed directly on the object images having been recorded with the radiation detector units 2a, 2b, and 2c, an accurate composed image will not be capable of being obtained.

Therefore, in this embodiment, as illustrated in FIG. 4, the image processing unit 5 takes the radiation detector unit 2b as a reference unit. Also, the image processing unit 5 performs image size enlargement processing on each of the image signals, which have been outputted from the radiation detector units 2a and 2c, and with an enlargement scale factor of b/a in accordance with the ratio between the distance from the X-ray source 8 to the radiation detector unit 2b and the distance from the X-ray source 8 to each of the radiation detector units 2a and 2c. Thereafter, the image processing unit 5 performs the image composing processing on the image signal, which has been outputted from the radiation detector unit 2b, and processed image signals, which have been obtained from the image size enlargement processing having been performed on the image signals having been outputted from the radiation detector units 2a and 2c. Therefore, with this embodiment, an accurate composed image is capable of being obtained.

Specifically, for example, the distance "b" from the X-ray source 8 to the radiation detector unit 2b may be equal to 1,800 mm. Also, the thickness of the radiation detector unit 2 may be equal to 30 mm. In such cases, the distance "a" from the X-ray source 8 to each of the radiation detector units 2a and 2c is equal to 1,770 mm. Therefore, in such cases, the enlargement scale factor is equal to 1.017.

Figure 6:
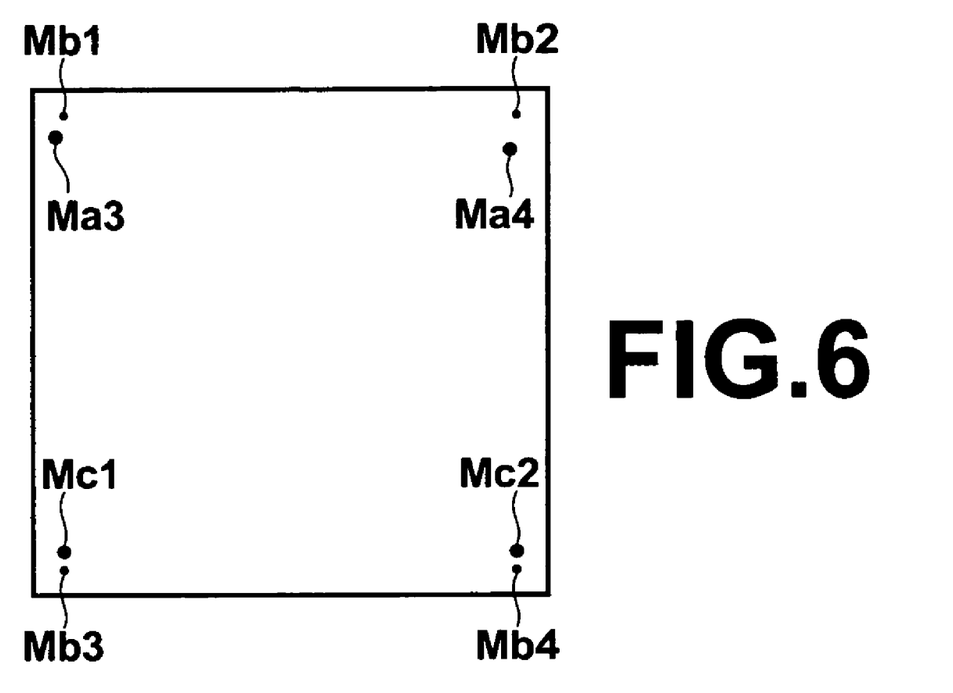
FIG. 6 is an explanatory view showing examples of image patterns of the markers (radiation absorbing members), which image patterns have been recorded by use of the radiation detector units.

As illustrated in FIG. 6, in the image having been recorded with the radiation detector unit 2b, which is located on the side remoter from the X-ray source 8 than the radiation detector units 2a and 2c are, image patterns of the markers Mb1, Mb2, Mb3, and Mb4, which are located in the radiation detector unit 2b, are embedded. Also, in the image having been recorded with the radiation detector unit 2b, the image patterns of the markers Ma3 and Ma4, which are located in the radiation detector unit 2a, are embedded at the positions in the vicinity of the top end region of the image. Further, in the image having been recorded with the radiation detector unit 2b, the image patterns of the markers Mc1 and Mc2, which are located in the radiation detector unit 2c, are embedded at the positions in the vicinity of the bottom end region of the image.

The positions of the markers Mb1 and Mb2, which are located in the radiation detector unit 2b, are already known. In cases where the image pattern of the marker Ma3, which is located in the radiation detector unit 2a, is embedded at the position shifted from the position of the image pattern of the marker Mb1, and the image pattern of the marker Ma4, which is located in the radiation detector unit 2a, is embedded at the position shifted from the position of the image pattern of the marker Mb2, the position of the radiation detector unit 2a may be adjusted by use of the dial meters 40a, 40b, and 40c and in accordance with the quantities of the shifts. In this manner, a tilt and a shift of the radiation detector unit 2a are capable of being eliminated.

Also, the positions of the markers Mb3 and Mb4, which are located in the radiation detector unit 2b, are already known. In cases where the image pattern of the marker Mc1, which is located in the radiation detector unit 2c, is embedded at the position shifted from the position of the image pattern of the marker Mb3, and the image pattern of the marker Mc2, which is located in the radiation detector unit 2c, is embedded at the position shifted from the position of the image pattern of the marker Mb4, the position of the radiation detector unit 2c may be adjusted by use of the dial meters 41a, 41b, and 41c and in accordance with the quantities of the shifts. In this manner, a tilt and a shift of the radiation detector unit 2c are capable of being eliminated.

In this embodiment, the image size enlargement processing with an enlargement scale factor of b/a is performed on each of the image signals, which have been outputted from the radiation detector units 2a and 2c. Alternatively, image size reduction processing with a reduction scale factor of a/b may be performed on the image signal, which has been outputted from the radiation detector unit 2b.

Further, each of the radiation detector units 2a and 2c may be located on the side remote from the X-ray source 8, and the radiation detector unit 2b may be located on the side close to the X-ray source 8.

The radiation imaging apparatus in accordance with the present invention is not limited to the embodiment described above and may be embodied in various other ways. For example, two radiation detector units may be utilized. Also, at least four radiation detector units may be utilized. Further, the radiation detector units maybe arrayed in two-dimensional directions.

What is claimed is:

1. A radiation imaging apparatus, comprising:
   i) a plurality of radiation detector units, each of which is provided with a solid-state radiation detector, the solid-state radiation detector being capable of recording image information when radiation carrying the image information is irradiated to the solid-state radiation detector, the solid-state radiation detector outputting an image signal representing the image information having been recorded in the solid-state radiation detector,
   ii) a radiation detector unit supporting section for supporting the plurality of the radiation detector units in a state, in which the plurality of the radiation detector units are located at different distances from a radiation source for irradiating the radiation to the plurality of the radiation detector units and are arrayed in a one-dimensional direction or in two-dimensional directions, and
   iii) image composing means for:
   performing image composing processing on the image signals, which have been outputted from the plurality of the radiation detector units, and in accordance with the array of the plurality of the radiation detector units, and thereby acquiring a composed image signal;
   taking one radiation detector unit, which is among the plurality of the radiation detector units, as a reference unit;
   performing image size enlargement or reduction processing on each of the image signals, which have been outputted from the radiation detector units other than the reference unit, and in accordance with a ratio between a distance from the radiation source to the reference unit and a distance from the radiation source to each of the radiation detector units other than the reference unit; and thereafter
   performing the image composing processing on the image signal, which has been outputted from the reference unit, and processed image signals, which have been obtained from the image size enlargement or reduction processing having been performed on the image signals having been outputted from the radiation detector units other than the reference unit.

2. An apparatus as defined in claim 1 wherein the radiation detector unit supporting section is provided with position adjusting means for adjusting the positions of the radiation detector units with respect to one another.

3. An apparatus as defined in claim 2 wherein the position adjusting means comprises dial meters.

4. An apparatus as defined in claim 3 wherein each of the radiation detector units is provided with a radiation absorbing member for indicating a reference position, which radiation absorbing member is located at an area in the vicinity of an outside periphery of the solid-state radiation detector constituting the radiation detector unit.

5. An apparatus as defined in claim 2 wherein each of the radiation detector units is provided with a radiation absorbing member for indicating a reference position, which radiation absorbing member is located at an area in the vicinity of an outside periphery of the solid-state radiation detector constituting the radiation detector unit.

* * * * *